United States Patent
Lee

(12) 
(10) Patent No.: US 6,600,092 B2
(45) Date of Patent: Jul. 29, 2003

(54) **PLANT SPECIES *SSAMCHOO* AND BREEDING METHOD THEREOF**

(76) Inventor: Kwanho Lee, 105-201 Hyungdae Hanjin Apt. Hwasoe-2 Dong, Jangan-Gu, Suwon-Si, Kyonggi-Do (KR)

( * ) Notice: Subject to any disclaimer, the term of this patent is extended or adjusted under 35 U.S.C. 154(b) by 0 days.

(21) Appl. No.: 09/731,718

(22) Filed: Dec. 8, 2000

(65) Prior Publication Data

US 2002/0040486 A1 Apr. 4, 2002

(30) Foreign Application Priority Data

Aug. 8, 2000 (KR) .......................................... 2000-45866
Sep. 18, 2000 (KR) .......................................... 2000-54639

(51) Int. Cl.⁷ .............................. A01H 1/00; A01H 1/04; A01H 1/08; A01H 5/00; A01H 5/10
(52) U.S. Cl. ........................ 800/306; 800/260; 800/266; 800/268; 800/269; 435/430.1
(58) Field of Search ................................. 800/306, 260, 800/266, 268, 269, 295, 298; 435/410, 430.1

(56) References Cited

PUBLICATIONS

Anonymous. Version 4, Jan. 2002. *Brassica lee* and *ssamchoo* search. 4 web pages pages. USDA–ARS GRIIN Taxonomy. http://www.ars–grin.gov/npgs/tax/index.html.*
Anonymous. Version 5, Nov. 2001. *Brassica lee, Brassica lee ssp. namai*, and *ssamchoo* search. The International Plant Names Index. 8 web pages. http://www.ipni.org/.*
Anonymous. Version 23, Aug. 2000. *Brassica lee* and *ssamchoo* search. The International Association of Plant Technology Registration of Plant Names Index. 6 web pages. http://bgbm.fu–berlin.de/iapt/.*
Jahier et al. 1989. Extraction of disomic addition lines of *Brassica napus–B. nigra*. Genome 32(3):408–413.*
Kalasa–Balicka et al. 1985. Characterization of synthetic *Brassica napus* L. (*B. campestris ssp. pekinensis cv Granaat x B.oleracea ssp. acephala cv.* Normal). Genetica Palonica 26(4):447–456.*
Namai et al. 1989. Inducing cytogenetic alterations by means of interspecific and iintergeneric hybridization in Brassica crops. Gamma Field Symposium 26:41–89.*
Nishi et al. 1980. Differentiation of Brassica crops in Asia and breeding of 'Hakuran', a newly synthesized leafy vegetable. pp133–150, In: Brassica Crops and Wild Allies (Editors Tsunoda, Hinata, and Gomes–Campo). Japan Sci. Soc. Press, Tokyo.*
Olsson et al 1960. Species crosses within the genus Brassica. II. Artificial *Brassica napus* L. Hereditas 46:351–396.*
Strauss et al. 1991. Development of B–genome chromosome addition lines of *B. napus* using different interspecific hybrids. Plant Breeding 106:209–214.*

* cited by examiner

Primary Examiner—David T. Fox
(74) Attorney, Agent, or Firm—Morrison & Foerster LLP

(57) ABSTRACT

The present invention relates to a novel plant species *ssamchoo* and to the breeding method thereof. As described through the above examples, the present novel plant species, "*ssamchoo*" which is obtained by aneuploidy crossing Chinese cabbage with cabbage and has the chromosome number of 2n=40 is an extremely valuable invention from the viewpoint of agriculture by virtue of the substitute for lettuce when its leaves are harvested piece by piece and the remarkable use for salad if it is folded into a loose-head.

3 Claims, 4 Drawing Sheets

Fig. 1

Year

1984 Chinese cabbage × Cabbage
   (2n=20, AA)     (2n=18, CC)
         ↓ Embryonic culture 1985     Amphihaploid
      (2n=19, AC)
       ↓ Colc. treatment
     Artificial *B.napus*
      (2n=38, AACC)
       ↓ Selfing 1986  Amphidiploid × Chinese cabbage
   (2n=38, AACC)   (2n=20, AA)
        ↓

1987   Sesquidiploid × Chinese cabbage
   ($B_1F_1$, 2n=29, AAC)  (2n=20, AA)
        ↓

1988     Aneuploid
   $B_2F_1$, 2n=25, 10 II (A)+5 I (C)
       ↓ Selfing, Selection 1989   $B_2F_2$, 2n=24, 10 II (A)+4 I (C)
       ↓ Selfing, Selection 1990   $B_2F_3$, 2n=40, 20 II (A+C)
       ↓ Selfing 1991   $B_2F_4$, 2n=40, 20 II (A+C)
       ↓ Selfing 1997   $B_2F_5$, 2n=40, 20 II (A+C) ------- [A]

PLANT SPECIES *SSAMCHOO* AND BREEDING METHOD THEREOF

BACKGROUND OF THE INVENTION

1. Field of the Invention

The present invention relates to a novel plant species *ssamchoo* and to the breeding method thereof. More particularly, the present invention relates to a novel plant species *ssamchoo* which was developed by aneuploid breeding method between Chinese cabbage and cabbage and to the breeding method of *ssamchoo*.

2. Description of Prior Art

In some cases, in Korea, Chinese cabbage is eaten uncooked, but in usual cases, eaten as kimchi. When eating cabbage as leaf-wrapped rice or fresh salad, the elliptical shape, rigid stalks and oval shapes of cabbage leaves are problems and not so convenient for eating. Though the above problem is not apparent in lettuces particularly in the case of lettuce-wrapped rice, it is not so suitable for salad, either.

Upon consideration of the above points, in order to obtain a novel plant species that can be used as a substitute for lettuce and as the material for salad, the inventors achieved the present invention *ssamchoo* in the way by crossing as seed parent the plant selected through 5th generation of aneuploid (2n=25) obtained by repeatedly crossing the sesquidiploid with Chinese cabbage, which was obtained by crossbreeding a hybrid between Chinese cabbage and cabbage with Chinese cabbage with as pollen parent the plant selected through 5th generation of aneuploid (2n=26) obtained by repeatedly crossing the sesquidiploid generation with Chinese cabbage, which was obtained by crossbreeding a hybrid between Chinese cabbage and cabbage with Chinese cabbage, and investigated the chromosome number of it to be 2n=40.

That is, the chromosome number of ordinary Chinese cabbage is 2n=20, the chromosome number of cabbage is 2n=18, the chromosome number of leaf mustard is 2n=36 and the chromosome number of rape is 2n=38, but that of novel plant species invented by the present inventor is 2n=40 and it is a nonexistent plant even now.

Consequently, the purpose of the present invention is to provide novel plant species developed from a hybrid between Chinese cabbage and cabbage with Chinese cabbage by a aneuploid breeding method.

Another purpose of the present invention is to provide the breeding method of the above novel plant species *ssamchoo*.

SUMMARY OF THE INVENTION

With the background in mind, the present invention is aimed to provide a novel plant species, *ssamchoo*.

Another object of the present invention is to provide the breeding method of a novel plant species, *ssamchoo*.

The purpose of the present invention was accomplished by developing the novel plant in the way of crossing $B_2F_5$ as seed parent selected through 5th generation of aneuploid (2n=25) obtained by repeatedly crossing the sesquidiploid with Chinese cabbage, which was obtained by crossbreeding a hybrid between Chinese cabbage and cabbage with Chinese cabbage with the plant as pollen parent selected through 5th generation of aneuploid (2n=26) obtained by repeatedly crossing the sesquidiploid with Chinese cabbage, which was obtained by crossbreeding a hybrid between Chinese cabbage and cabbage with Chinese cabbage, and accomplished by investigating the feature of novel plant species and then by growing plant having the genetically equal chromosome number of 2n=40 from tissue culture in part.

BRIEF DESCRIPTION OF THE DRAWINGS

The above and other objects and aspects of the invention will become apparent from the following description of embodiments with reference to the accompanying drawings in which:

FIG. 1 and FIG. 2 are breeding diagrams showing the process of obtaining the present invention *ssamchoo* using Chinese cabbages and cabbages collected from 1984 to 1997;

DETAIED DESCRIPTION OF THE INVENTION

The present invention pertains to a novel plant species *ssamchoo* and to the breeding method which are composed of following the steps of; obtaining a hybrid between Chinese cabbage and cabbage; breeding the above hybrid by means of aneuploid breeding method and naming it "*ssamchoo*"; after culturing *ssamchoo*, investigating the morphological and cytological features; tissue culturing in part of the present invention *ssamchoo*, and obtaining genetically equal plants.

A better understanding of the present invention may be obtained through the following examples which are set forth to illustrate, but are not to be construed as the limit of the present invention.

EXAMPLE 1

Breeding of Novel Plant Species *ssamchoo*

Figure 2:
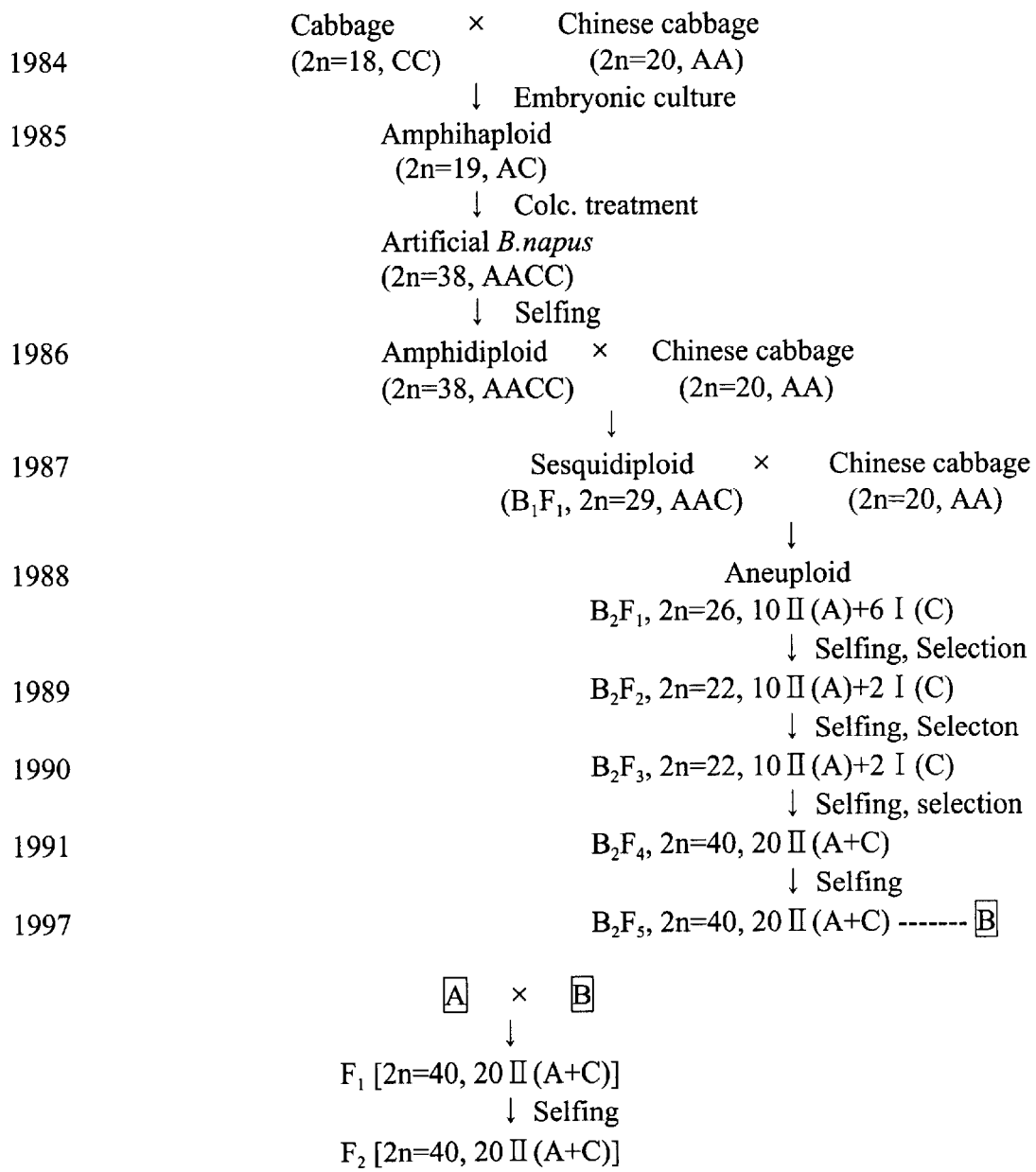

This example had been accomplished from 1987 to 1997 using Chinese cabbages and cabbages collected in 1984. Namely, as breeding diagram of FIG. 1 and FIG. 2, Chinese cabbage was crossed with cabbage to produec a hybrid, which was treated with colchicine in order to stabilize the hybrid. After the above hybrid was crossed with Chinese cabbage, sesquidiploid plant was crossed with Chinese cabbage, then many aneuploids (2n=25) were obtained. From among these, cabbage lines were selected by observation of chromosomes, identification of non-compatibility, and fertility of pollens and seed. After that, $B_2F_1$ aneuploid (2n=25) selected were crossed, from which many plants were obtained. Continuously, upon obtaining $B_2F_2$, $B_2F_3$ and $B_2F_4$ a cause of acclimation of family, new family coincided with the object of breeding were selected and crossed. Finally, *ssamchoo* were produced.

Figure 3:
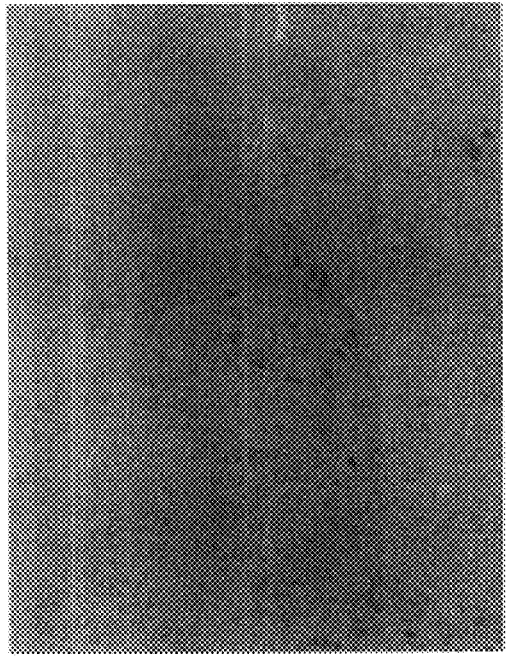
FIG. 3 is the photograph showing the result of making observation and identifying plant chromosomes being reduced in the first meiotic division 2n=40, with an optical microscope.
Figure 4:
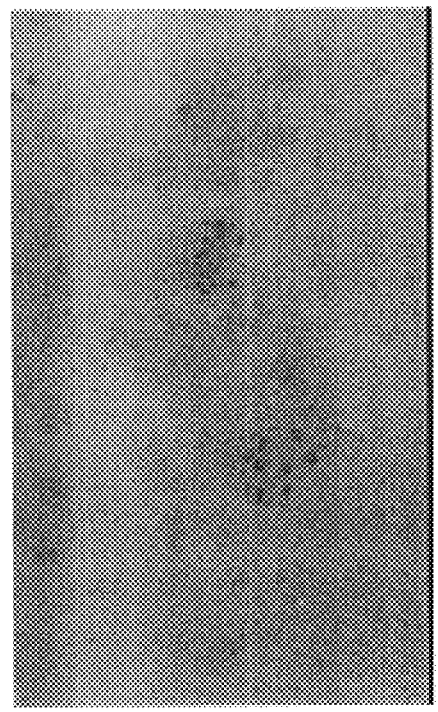
FIG. 4 is the photograph showing the result of making observation and identifying plant chromosomes being reduced in the second meiotic division 2n=40, with an optical microscope.

Table 1 is the fertility chart of the breeding materials. FIG. 3 is the photograph showing the result of making observation and identifying plant chromosomes being reduced in the first meiotic divisions, 2n=40 with an optical microscope. As shown in FIG. 1, chromosome number is 2n=40. FIG. 4 is the photograph showing the result of making observation and identifying plant chromosomes being reduced in the second meiotic division with an optical microscope, also chromosome number is 2n=40.

TABLE 1

The fertility chart of the breeding materials

| Name of Breed (line) | Fertility | Name of Breed (line) | Fertility |
|---|---|---|---|
| Cabbage | 8.9 (%) | $B_2F_4$ | 6.8 |
| Chinese cabbage | 32.0 | $B_2F_5$ ... A | 0.0 |
| Chinese cabbage | 31.5 | Aneuploid ($B_2F_1$, 2n = 26) | 11.0 |
| Chinese cabbage | 24.0 | $B_2F_2$ | 22.0 |
| Chinese cabbage | 32.0 | $B_2F_3$ | 12.7 |
| Amphidiploid (2n = 38, AACC) | 4.5 | $B_2F_4$ | 11.1 |
| Sesquidiploid (2n = 29, AAC) | 29.7 | $B_2F_5$ ... B | 0.0 |
| Aneuploid ($B_2F_1$, 2n = 25) | 32.4 | $F_1$ | 19.8 |
| $B_2F_2$ | 32.5 | $F_2$ | 11.8 |
| $B_2F_3$ | 1.6 | | |

EXAMPLE 2

Culturing of the Present Invention Novel Plant "ssamchoo"

Figure 5:
FIG. 5 is the photograph showing the external appearance of the present invention, a novel species *ssamchoo* cultivated in the soil.
Figure 6:
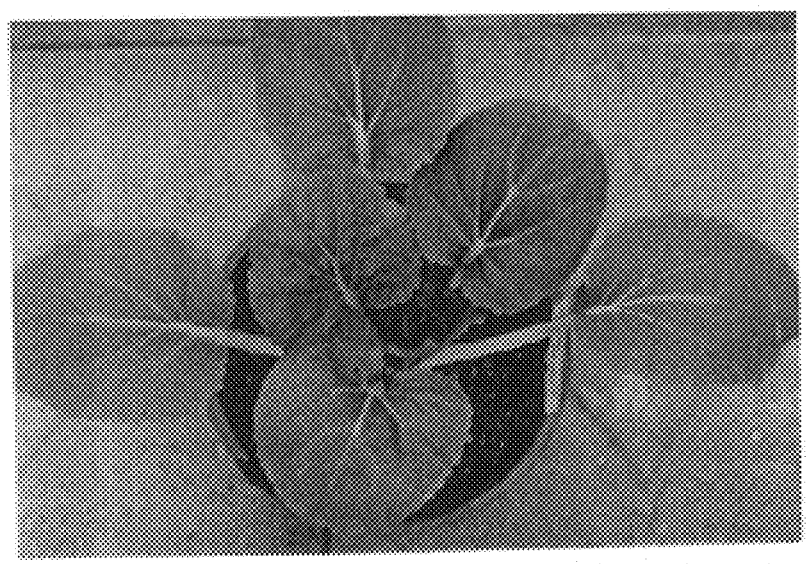
FIG. 6 is the photograph showing the external appearance of the present invention, a novel species *ssamchoo* cultivated in the flowerpot.

"Ssamchoo" obtained from the above example 1 was cultivated at 13° C. and over in order to prevent flower bud formation at low temperature. Lime and borax were added to initial manure, NaCl 0.3% (60 g per $H_2O$ 20 L) was sprayed about three times at 5 days intervals on leaves according to the lime deficiency. A field was maintained not too dry and not too wet either. In order to avoid an attack of plant diseases such as flacherie, the harvest time was selected. And, the manures were controlled so as not to contact plant diseases such as downy mildew due to nutrient deficiency. FIG. 5 is the photograph showing the external appearance of the present invention novel species ssamchoo cultivated in the soil.

EXAMPLE 3

A Specific Character of ssamchoo

The present example shows the characteristics of the present invention "ssamchoo" and compares "ssamchoo" with Pyungchong 1, based on the size of plant, the shape of leaves, the width of the midrib and the head.

Referring to Table 2, the height of Pyungchong 1 is middle, the shape of external leaves is egg shape, the width of the midrib is narrow and the head is loose-head. Pyungchong 1 has highly developed petioles and elliptical leaves. It is possible to produce Ssamchoo during the whole year-round.

TABLE 2

The specific characteristics of the present invention ssamchoo

| Character | Phenotype | Grade |
|---|---|---|
| Plant: height (1)* | Short | 3 [] |
| | Middle | 5 [0] |
| | Tall | 7 [] |
| External leaves: shape (4) | egg shape | 1 [0] |
| | wide egg shape | 2 [] |
| | wide egg shape and wide oval shape | 3 [] |
| | wide oval shape | 4 [] |
| | oval shape | 5 [] |
| External leaves: the width of the midrib (16) | Narrow | 3 [] |
| | Middle | 5 [] |
| | Wide | 7 [] |
| Head: head formation | head formation | 1 [] |
| | loose-head formation | 2 [0] |
| | non-head formation | 3 [] |

[Note]
*: the character number of the test guidebook

Table 3. shows the result of comparison with Pyungchong 1. The height of ssamchoo is middle, 36.4 cm, external leaves lies a little, external leaves are small, the shape of external leaves is egg shape, and unevenness of external leaves is feeble. And then, external leaves is green and a little bright, glosses are middle, longitudinal section of external leaves is flat, edges of external leaves have a little wave shape and saw tooth. The cross section of the midrib is convex and the width of the midrib is narrow. The head of ssamchoo is open, the color of external leaves is light green, brightness is middle. The inside color of head is white, the hardness of the head is weak, formative periods of head and maturation period is late. One head has 60 wrapper sheets, weight of head is light and weight is about 1.3 kg.

The novel plant species ssamchoo was named Brassica lee L. ssp. namai cv. Ssamchoo and deposited in Korean Collection for Type Cultures, Korean Research Institute of Bioscience and Biotechnology on Sep. 8, 2000 at Accession No. KCTC 0856BP.

TABLE 3

Character comparison "ssamchoo" with general Chinese cabbage.

| | | Phenotype | | | | | | | | Application plants | | Contrastive plants | |
|---|---|---|---|---|---|---|---|---|---|---|---|---|---|
| No. | Character of external leave | 1 | 2 | 3 | 4 | 5 | 6 | 7 | 8 | 9 | No. | Height | No | Height |
| 1 | Plant: Height | | | Short | | Middle | | Tall | | | 3 | 36.4 cm | 5 | 45.7 cm |
| 2 | Position | | | Stand | | A little lie | | Lie | | | 5 | | 6 | |
| 3 | Size | | | Small | | Middle | | Large | | | 3 | | 5 | |

TABLE 3-continued

Character comparison "ssamchoo" with general Chinese cabbage.

| No. | Character of external leave | Phenotype 1 | 2 | 3 | 4 | 5 | 6 | 7 | 8 | 9 | Application plants No. | Height | Contrastive plants No | Height |
|---|---|---|---|---|---|---|---|---|---|---|---|---|---|---|
| 4 | Shape | Egg shape | Wide egg shape | Wide egg + wide oval shape | Wide oval shape | Oval shape | | | | | 1 | | 3 | |
| 5 | Unevenness | | | Smooth | | Middle | | Serious | | | 3 | | 4 | |
| 6 | Size of unevenness | | | Small | | Middle | | Large | | | 3 | | 5 | |
| 7 | Color | Yellow Green | Green | Gray green | | | | | | | 2 | | 2 | |
| 8 | Brightness of color | | | Light | | Middle | | Dark | | | 4 | | 4 | |
| 9 | Gloss | | | Quiet | | Middle | | Strong | | | 5 | | 4 | |
| 10.1 | Hair | Few | | | | | | | | Being | 9 | | 9 | |
| 10.2 | Amount of hair | | | Few | | Middle | | Many | | | 5 | | 5 | |
| 11 | Longitudinal section | | | Concave | | Flat | | Convex | | | 5 | | 3 | |
| 12 | Wave shape of edge | Little | | a little | | Middle | | Much | | Very much | 3 | | 6 | |
| 13 | Saw tooth of edge | Little | | a little | | Middle | | Much | | Very much | 3 | | 6 | |
| 14 | Sharp saw tooth of edge | Little | | a little | | Middle | | Much | | Very much | 1 | | 3 | |
| 15 | Crosscut of main vein | Concave | Middle | Convex | | | | | | | 3 | | 2 | |
| 16 | Width of main vein | | | Narrow | | Middle | | Wide | | | 1 | | 5 | |
| 17 | Head: height | | | Short | | Middle | | Tall | | | | | 5 | |
| 18 | Head: width | | | Narrow | | Middle | | Wide | | | | | 5 | |
| 19 | Head: a longitudinal section | Oval + square shape | Oval shape | Wide oval shape | Round shape | Egg shape | Wide egg shape | | | | | | 3 | |
| 20 | Head: head formation | Non-head | | Open | | Loose-head | | Closed | | | 3 | | 6 | |
| 21 | Head: color of external leaves | Yellow | Light green | Green | | | | | | | 2 | | 2 | |
| 22 | Head: color brightness of external leaves | | | Light | | Middle | | Dark | | | 5 | | 3 | |
| 23 | Head: unevenness | Little | | a little | | Middle | | Much | | Very much | | | 3 | |
| 24 | Head: color of inside | White | Light yellow | Yellow | Deep yellow | Orange | Light green | | | | 1 | | 1 | |
| 25 | Head: Hardness | Very weak | | Weak | | Middle | | Hard | | Very hard | 3 | | 7 | |
| 26 | Head: length of the pith | | | Short | | Middle | | Long | | | | | 4 | 6.2 cm |
| 27.1 | Head: formative period | Very fast | | Fast | | Middle | | Late | | Very late | 8 | | 5 | |
| 27.2 | Maturation period | Very fast | | Fast | | Middle | | Late | | Very late | 8 | | 5 | |
| 28 | Head: period of stalking | | | Fast | | Middle | | Late | | | 9 | | 5 | |
| 29 | Number of wrapper | | | a few | | Middle | | Many | | | 4 | 60 sheets | 6 | |
| 30 | Weight of head | | | Light | | Middle | | Heavy | | | 3 | 1.3 kg | 5 | 2.6 kg |

EXAMPLE 4

The Tissue Culturing of *ssamchoo*

The present example shows the tissue culturing of *ssamchoo* (*Brassica lee* L. ssp. *namai*) (KCTC 0856BP) as a method of propagating by asexual reproduction, and genetically equal plants (2n=40) were produced.

In order to culture *ssamchoo* tissues, the *ssamchoo*'s seeds were sowed on MS medium (plant growth regulator free). One week later, the cotyledons were collected and transferred on MS medium supplemented with NAA (a kind of auxin) 1–2 mg/mL+BA (a kind of cytokinin) 6–8 mg/mL.

What is claimed is:
1. A method of making Brassica hybrid seed comprising:
   (a) crossing a Chinese cabbage female parent with chromosome counts of 2N=20, with a Cabbage male parent with chromosome counts of 2N=18, to make F1 progeny embryos;

(b) collecting said F1 progeny embryos, tissue culturing said embryos, growing said embryos into F1 progeny plantlets and treating said plantlets with colchicine, karyotype characterizing said treated plantlets; and selecting for an amphidiploid F1 plantlet with chromosome counts of 2N=38;

(c) growing said amphidiploid F1 plantlet with chromosome counts of 2N=38 into a mature F1 plant; selfing said amphidiploid mature F1 plant, collecting F2 progeny seed, growing said seed into F2 plants and plantlets; karyotype characterizing said F2 plants or plantlets, and selecting for an amphidiploid F2 plant or plantlet with chromosome counts of 2N=38;

(d) crossing said amphidiploid F2 plant or plantlet with chromosome counts 2N=38 as a female parent, with Chinese cabbage with chromosome counts of 2N=20 as a male parent, collecting F3 progeny seed, growing said seed into F3 plants or plantlets, karyotype characterizing said F3 plants or plantlets, and selecting for a sesquidiploid F3 plant or plantlet with chromosome counts of 2N=29;

(e) crossing said sesquidiploid F3 plant or plantlet with chromosome counts of 2N=29 as a female parent, with Chinese cabbage with chromosome counts of 2N=20 as a male parent, collecting F3 progeny seed, growing said seed into F4 plants or plantlets; karyotype characterizing said F4 plants or plantlets, evaluating plantlets or plants for the traits of leaf morphology and developmental time to bolting under standard growth conditions, and selecting for an F4 aneuploid plant with chromosome counts of 2N=25 and comprises the traits of round leaves with petioles and late developmental time to bolting under standard growth conditions;

(f) selfing said selected F4 aneuploid plant, collecting F5 seed, growing said F5 seed into F5 plants or plantlets; karyotype characterizing said F5 plants or plantlets, and selecting for an F5 plant or plantlet with a chromosome count of 2N=24;

(g) selfing said selected F5 aneuploid plant, collecting F6 seed, growing said F6 seed into F6 plants or plantlets under standard growth conditions, karyotype characterizing said F6 plants or plantlets, evaluating F6 plantlets or plants for the traits of leaf morphology and developmental time to bolting under standard growth conditions, and selecting for an F6 plant with chromosome counts of 2N=40 and comprises the traits of round leaves with petioles and late developmental time to bolting under standard growth conditions;

(h) selfing said selected F6 plant with a chromosome count of 2N=40, collecting F7 seed, growing said F7 seed into F7 plants or plantlets under standard growth conditions, karyotype characterizing said F7 plants or plantlets, evaluating F7 plantlets or plants for the traits of leaf morphology and developmental time to bolting under standard growth conditions, and selecting for an F7 plant with chromosome counts of 2N=40 and comprises round leaves with petioles and late developmental time to bolting under standard growth conditions;

(i) repeating the selfing, characterization, evaluation, and steps of (h), utilizing the F7 plant with a chromosome count of 2N=40;

(j) selecting an FS plant from plants made by the steps of (a)–(i), selecting for a plant with chromosome counts of 2N=40 that comprises the traits of round leaves with petioles and late developmental time bolting under standard growth conditions;

(k) crossing a cabbage female parent with 2N=18, with a Chinese cabbage male parent with chromosome counts of 2N=20, to make F1 progeny embryos;

(l) collecting said F1 progeny embryos, tissue culturing said embryos, growing said embryos into F1 progeny plantlets and treating said plantlets with colchicine, karyotype characterizing said treated plantlets; and selecting for an amphidiploid F1 plantlet with chromosome counts of 2N=38;

(m) growing said amphidiploid F1 plantlet with chromosome counts of 2N=38 into a mature F1 plant; selfing said amphidiploid mature F1 plant, collecting F2 progeny seed, growing said seed into F2 plants or plantlets; karyotype characterizing said F2 plants or plantlets, and selecting for an amphidiploid F2 plant or plantlet with chromosome counts of 2N=38;

(n) crossing said amphidiploid F2 plant or plantlet with chromosome counts of 2N=38 as a female parent, with Chinese cabbage with chromosome counts of 2N=20 as a male parent, collecting F3 progeny seed, growing said seed into F3 plants or plantlets, karyotype characterizing said F3 plants or plantlets, and selecting for a sesquidiploid F3 plant or plantlet with chromosome counts of 2N=29;

(o) crossing said sesquidiploid F3 plant or plantlet with chromosome counts of 2N=29 as a female parent, with Chinese cabbage with chromosome counts of 2N=20 as a male parent, collecting F3 progeny seed, growing said seed into F4 plants or plantlets; karyotype characterizing said F4 plants or plantlets, evaluating plantlets or plants for the traits of leaf morphology and developmental time to bolting under standard growth conditions, and selecting for an F4 aneuploid plant with chromosome counts of 2N=26 and comprises the traits of round leaves with petioles and late developmental time to bolting under standard growth conditions;

(p) selfing said selected F4 aneuploid plant, collecting F5 seed, growing said F5 seed into F5 plants or plantlets; karyotype characterizing said F5 plants or plantlets, and selecting for an F5 plant or plantlet with a chromosome count of 2N=22;

(q) selfing said selected F5 aneuploid plant, collecting F6 seed, growing said F6 seed into F6 plants or plantlets under standard growth conditions, karyotype characterizing said F6 plants or plantlets, evaluating F6 plantlets or plants for the traits of leaf morphology and developmental time to bolting under standard growth conditions, and selecting for an F6 plant with chromosome counts of 2N=40 and comprises the traits of round leaves with petioles and late developmental time to bolting under standard growth conditions;

(r) selfing said selected F6 plant with a chromosome count of 2N=40, collecting F7 seed, growing said F7 seed into F7 plants or plantlets under standard growth conditions, karyotype characterizing said F7 plants or plantlets, evaluating F7 plantlets or plants for the traits of leaf morphology and developmental time to bolting under standard growth conditions, and selecting for an F7 plant with chromosome counts of 2N=40 and comprises the traits of round leaves with petioles and late developmental time to bolting under standard growth conditions;

(s) repeating the selfing, characterization, evaluation, and steps of (r), utilizing the F7 plant with a chromosome count of 2N=40;

(t) selecting an F8 plant from plants made by the steps of (k)–(s), selecting for a plant with a chromosome count of 2N=40 and comprises the traits of round leaves with petioles and late developmental time to bolting under standard growth conditions;

(u) crossing the F8 plant selected in step (I), as a female parent, with a male parent of the F8 plant selected in step (t);

(v) collecting seed produced from the cross of step (u), growing said seed into a new F1 hybrid plant line under standard growth conditions, karyotype characterizing said new F1 hybrid plants, and evaluating new F1 hybrid plants for the trait of oval, egg shaped leaves;

(w) selecting new F1 hybrid plants with a chromosome count of 2N=40 and comprising the trait of oval, egg-shaped leaves;

(x) selfing the plants selected in step (w); and (y) collecting Brassica hybrid seed from the selfed hybrid plants of step (x).

2. Seed of a Brassica hybrid plant, deposited as KCTC Accession. No. 0856BP.

3. Plants grown from the seed of claim 2, with chromosome number of 2N=40, and comprising a trait of oval, egg-shaped leaves.

* * * * *